US008790920B2

(12) United States Patent
Freyman (10) Patent No.: US 8,790,920 B2
(45) Date of Patent: Jul. 29, 2014

(54) DECELLULARIZED BONE MARROW EXTRACELLULAR MATRIX (75) Inventor: Toby Freyman, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1308 days.

(21) Appl. No.: 12/021,625

(22) Filed: Jan. 29, 2008

(65) Prior Publication Data
US 2008/0124374 A1 May 29, 2008

Related U.S. Application Data (62) Division of application No. 10/622,674, filed on Jul. 17, 2003, now Pat. No. 7,326,571.

(51) Int. Cl.
C12N 5/00 (2006.01)
(52) U.S. Cl.
USPC ........... 435/325; 435/366; 435/395; 424/400; 424/422
(58) Field of Classification Search
USPC ........... 435/372, 325, 366, 395; 424/400, 422
See application file for complete search history.

(56) References Cited

U.S. PATENT DOCUMENTS

| | | |
|---|---|---|
| 4,314,565 A | 2/1982 | Lee |
| 4,481,946 A | 11/1984 | Altshuler et al. |
| 4,486,188 A | 12/1984 | Altshuler et al. |
| 4,513,754 A | 4/1985 | Lee |
| 4,526,938 A | 7/1985 | Churchill et al. |
| 4,630,616 A | 12/1986 | Tretinyak |
| 4,655,771 A | 4/1987 | Wallsten |
| 4,664,128 A | 5/1987 | Lee |
| 4,954,126 A | 9/1990 | Wallsten |
| 5,012,818 A | 5/1991 | Joishy |
| 5,061,275 A | 10/1991 | Wallsten et al. |
| 5,082,670 A | 1/1992 | Gage et al. |
| 5,102,417 A | 4/1992 | Palmaz |
| 5,128,326 A | 7/1992 | Balazs et al. |
| 5,192,312 A | 3/1993 | Orton |
| 5,257,632 A | 11/1993 | Turkel et al. |
| 5,331,972 A | 7/1994 | Wadhwani et al. |
| 5,449,373 A | 9/1995 | Pinchasik et al. |
| 5,613,982 A | 3/1997 | Goldstein |
| 5,632,778 A | 5/1997 | Goldstein |
| 5,650,148 A | 7/1997 | Gage et al. |
| 5,679,377 A | 10/1997 | Bernstein et al. |
| 5,762,926 A | 6/1998 | Gage et al. |
| 5,800,537 A | 9/1998 | Bell |
| 5,830,708 A | 11/1998 | Naughton |
| 5,843,182 A | 12/1998 | Goldstein |
| 5,899,936 A | 5/1999 | Goldstein |
| 5,912,015 A | 6/1999 | Bernstein et al. |
| 5,916,597 A | 6/1999 | Lee et al. |
| 5,989,463 A | 11/1999 | Tracy et al. |
| 6,082,364 A | 7/2000 | Balian et al. |
| 6,241,981 B1 | 6/2001 | Cobb et al. |
| 6,656,916 B1 | 12/2003 | Schwarz et al. |
| 7,087,089 B2 | 8/2006 | Patel et al. |
| 2002/0077592 A1* | 6/2002 | Barry ........................ 604/96.01 |
| 2002/0082679 A1 | 6/2002 | Sirhan et al. |
| 2002/0082682 A1* | 6/2002 | Barclay et al. ............... 623/1.22 |
| 2002/0115208 A1 | 8/2002 | Mitchell et al. |
| 2003/0143207 A1 | 7/2003 | Livesey et al. |
| 2004/0022864 A1 | 2/2004 | Freyman et al. |
| 2004/0142014 A1 | 7/2004 | Litvack et al. |
| 2004/0175366 A1 | 9/2004 | Badylak |
| 2004/0249359 A1 | 12/2004 | Palasis et al. |
| 2005/0002986 A1 | 1/2005 | Falotico et al. |
| 2005/0013870 A1 | 1/2005 | Freyman et al. |
| 2005/0043678 A1 | 2/2005 | Freyman et al. |
| 2005/0158450 A1 | 7/2005 | Palasis et al. |
| 2005/0181016 A1 | 8/2005 | Freyman et al. |
| 2005/0233443 A1 | 10/2005 | Freyman |
| 2006/0029720 A1 | 2/2006 | Panos et al. |
| 2007/0005011 A1 | 1/2007 | Freyman et al. |
| 2007/0055352 A1 | 3/2007 | Naimark et al. |
| 2007/0065414 A1 | 3/2007 | Freyman et al. |
| 2007/0178137 A1 | 8/2007 | Freyman et al. |
| 2007/0219526 A1 | 9/2007 | Freyman |
| 2008/0085294 A1 | 4/2008 | Freyman et al. |
| 2008/0183143 A1 | 7/2008 | Palasis et al. |
| 2008/0260798 A1 | 10/2008 | Freyman et al. |
| 2009/0138074 A1 | 5/2009 | Freyman et al. |

FOREIGN PATENT DOCUMENTS

| | | |
|---|---|---|
| WO | WO 90/13332 | 11/1990 |
| WO | WO 91/05548 | 5/1991 |
| WO | WO 94/16646 | 8/1994 |
| WO | WO 96/20698 | 7/1996 |
| WO | WO 97/18842 | 5/1997 |
| WO | 9839035 A1 | 9/1998 |
| WO | WO 99/15154 | 4/1999 |
| WO | WO 99/20253 | 4/1999 |
| WO | WO 99/30648 | 6/1999 |
| WO | WO 99/43270 | 9/1999 |

(Continued)

OTHER PUBLICATIONS

Angele et al., 1999, "Engineering of osteochondral tissue with bone marrow mesenchymal progenitor cells in a derivatized hyaluronan-gelatin composite sponge." Tissue Eng.: 5(6):545-54.
Asawakarn T. et al., 2001, "Effects of the membrane dipole potential on the interaction of saquinavir with phospholipid membranes and plasma membrane receptors of Caco-2 cells." J Biol Chem.: 276(42):38457-63.

(Continued)

Primary Examiner — Ruth Davis
(74) Attorney, Agent, or Firm — Fish & Richardson P.C.

(57) ABSTRACT

The invention is directed to compositions comprising decellularized bone marrow extracellular matrix and uses thereof. Methods for repairing or regenerating defective, diseased, damaged or ischemic tissues or organs in a subject, preferably a human, using the decellularized bone marrow extracellular matrix of the invention are also provided. The invention is further directed to a medical device, preferably a stent or an artificial heart, and biocompatible materials, preferably a tissue regeneration scaffold, comprising decellularized bone marrow extracellular matrix for implantation into a subject.

19 Claims, 1 Drawing Sheet

(56) References Cited

FOREIGN PATENT DOCUMENTS

| WO | 9955379 A1 | 11/1999 |
| WO | WO 91/18972 | 12/1999 |
| WO | WO 99/61080 | 12/1999 |
| WO | WO 01/03750 | 1/2001 |
| WO | WO 01/32129 | 5/2001 |

OTHER PUBLICATIONS

Badylak et al., 2001, "Marrow-derived cells populate scaffolds composed of xenogeneic extracellular matrix." Exp Hematol., 29(11):1310-8.
Bleiberg et al., 1987, "New bone formation and bone marrow differentiation induced in rats by extracellular bone matrix implantation: effect of local preirradiation on the process." Exp Hematol., 15(4):309-15.
Buchwald et al., 1980, "Long-term, continuous intravenous heparin administration by an implantable infusion pump in ambulatory patients with recurrent venous thrombosis." Surgery., 88(4):507-16.
Cleek et al., 1997, "Biodegradable Polymeric Carriers for a bFGF Antibody for Cardiovascular Application." Pro. Int'l. Symp. Control. Rel. Bioact. Mater., 24:853-854.
Dichek D. et al., 1989, "Seeding of intravascular stents with genetically engineered endothelial cells." Circulation., 80(5):1347-53.
During et al., 1989, "Controlled release of dopamine from a polymeric brain implant: in vivo characterization." Ann Neurol., 25(4):351-6.
Hodges A. and Koury M., 1996, "Needle aspiration and biopsy in the diagnosis and monitoring of bone marrow diseases." Clin Lab Sci., 9(6):349-53.
Howard et al., 1989, "Intracerebral drug delivery in rats with lesion-induced memory deficits." J Neurosurg., 71(1):105-12.
Ino T. et al., 1997, "Dilation mechanism, causes of restenosis and stenting in balloon coarctation angioplasty." Acta Paediatr., 86(4):367-71.
Jiang et al., 2002, "Multipotent progenitor cells can be isolated from postnatal murine bone marrow, muscle, and brain," Exp. Hematol., 30:826-04.
Lam et al., 1997, "Microencapsulation of recombinant humanized monoclonal antibody for local delivery," Proc. Int'l. Symp. Control. Rel. Bioact. Mater., 24:759-60.
Langer and Peppas, 1983, "Chemical and physical structure of polymers as carriers for controlled release of bioactive agents: A review." J. Macromol, Sci. Rev. Macromol. Chem., 23(1):61-126.
Langer, 1990, "New methods of drug delivery," Science, 249:1527-33.
Lee et al., 1999, "Comparison of bone marrow extracellular matrices." Biochemica et Biophysica Acta., 1428, 300-304.
Levy et al., 1985, "Inhibition of calcification of bioprosthetic heart valves by local controlled-release diphosphonate." Science, 228(4696):190-2.
Lodie et al., 2002, "Systematic analysis of reportedly distinct populations of multipotent bone marrow-derived stem cells reveals a lack of distinction." Tissue Eng., 8(5):739-51.
Lupton J. and Alster T., 2000, "Cutaneous hypersensitivity reaction to injectable hyaluronic acid gel." Dermatol Surg., 26(2):135-7.
Ning et al., 1996, "Intratumoral radioimmunotherapy of a human colon cancer xenograft using a sustained-release gel." Radiotherapy & Oncology, 39:179-89.
Oliver R. et al., 1976, "Histological studies of subcutaneous and intraperitoneal implants of trypsin-prepared dermal collagen allografts in the rat." Clin Orthop Relat Res., (115):291-02.
Oliver R. et al., 1980, "Effect of aldehyde cross-linking on human dermal collagen implants in the rat." Br. J. Exp. Path., 61:544-49.
Oliver R. et al., 1981, "Hydroxyproline turnover in dermal collagen grafts in reconstructed skin wounds in the rat." Conn. Tissue Res., 9:59-62.
Olsvik O. et al., 1994, "Magnetic separation techniques in diagnostic microbiology." Clin Microbiol Rev., 7(1):43-54.
Paul et al., 1991, "Stromal Cell-Associated Hematopoiesis: Immortalization and Characterization of a Primate Bone Marrow-Derived Stromal Cell Line," Blood, 77(8):1723-33.
Peters et al., 1993, "Ovine bone marrow extracellular matrix and soluble protein extraction: Fetuin amino terminus microheterogeneity." The American Journal of the Medical Sciences, 285-294.
Pittenger et al., 1999, "Multilineage potential of adult human mesenchymal stem cells," Science, 2;284(541 1):143-47.
Sadovnikova et al., 1991, "Induction of hematopoietic microenvironment by the extracellular matrix from long-term bone marrow cultures." Ann Hematol, 62(5):160-4.
Saudek et al., 1989, "A preliminary trial of the programmable implantable medication system for insulin delivery." N. Engl J Med., 321(9):574-9.
Schmidt C. and Baier J., 2000, "Acellular vascular tissues: natural biomaterials for tissue repair and tissue engineering." Biomaterials., 21(22):2215-31.
Sefton, 1987, "Implantable pumps." CRC Crit. Ref. Biomed. Eng., 14(3):201-40.
Song et al., 1995, "Antibody mediated lung targeting of long-circulating emulsions." PDA Journal of Pharmaceutical Science & Technology, 50:372-397.
Sugita et al., 1994, "Prolonged impairment of very late activating antigen-mediated T cell proliferation via the CD3 pathway after T cell-depleted allogeneic bone marrow transplantation." J Clin Invest., 94(2):481-8.
Van Damme A. et al., 2002, "Bone marrow stromal cells as targets for gene therapy." Curr Gene Ther., 2(2):195-209.
Verfaillie C. et al., 2002, "Stem cells: Hype and Reality." Hematology (Am Soc Hematol Educ Program), 369-91.
Vituri et al., 2000, "Alterations in proteins of bone marrow extracellular matrix in undernourished mice", Braz. J. Med. Biol. Res., 22(8), 890-895.
Wu and Wu, 1987, "Receptor-mediated in vitro gene transformation by a soluble DNA carrier system." J Biol Chem., 262(10):4429-32.
Badylak et al., "Morphologic study of small intestinal submucosa as a body wall repair device," Journal of Surgical Research, 103(2): 190-202, 2002.
Badylak et al., "Small intestinal submucosa: A substrate for in vitro cell growth," Journal of Biomaterials Science Polymer Edition, 9(8):863-878, 1998.
Badylak et al., "Strength over time of a resorbable bioscaffold for body wall repair in a dog model," Journal of Surgical Research, 99(2):282-287, 2001.
Verma et al., "Gene Therapy: Twenty-First Century Medicine," Annu. Rev. Biochem. 74:711-738, 2005.
Goncalves, M., "A concise peer into the background, initial thoughts and practices of human gene therapy," BioEssays 27:506-517, 2005.
Romano et al., "Latest developments in gene transfer technology," Stem Cells 18:19-39, 2000.
Dang et al, "Gene therapy and translational cancer research," Clin. Cancer Res. 54:471-474, 1999.
Vituri et al., "Alterations in proteins of bone marrow extracellular matrix in undernourished mice," Brazilian Journal of Medical and Biological Research, 33:889-895, 2000.
Verma et al, "Gene therapy-promises, problems and prospects," Nature 389:239-242, 1997.
Voytik-Harbin et al., "Small intestinal submocosa: A tissue-derived extracellular matrix that promotes tissue-specific growth and differentiation of cells in vitro," Tissue Engineering, 4(2): 157-174, 1998.
Zantop et al., "Extracellular matrix scaffolds are repopulated by bone marrow-derived cells in a mouse model of achilles tendon reconstruction," J. Orthop. Res., 24 (6): 1299-1309, 2006.
Badylak, Xenogeneic extracellular matrix as a scaffold for tissue construction, Transplant Immunology 12 (2004), pp. 367-377.
Badylak, The extracellular matrix as a biologic scaffold material, Biomaterials, 28 (2007), pp. 3587-3593.
Robinson et al., Extracellular matrix scaffold for cardiac repair, Circulation, 112 (9 Suppl., 2005), pp. I135-I143.

* cited by examiner

DECELLULARIZED BONE MARROW EXTRACELLULAR MATRIX

This application is a divisional of U.S. application Ser. No. 10/622,674, filed Jul. 17, 2003 now U.S. Pat. No. 7,326,571, the entire disclosure of which is incorporated herein by reference in its entirety.

1. FIELD OF THE INVENTION

The invention relates generally to decellularized bone marrow extracellular matrix, as well as methods for the production and use thereof. In particular, the invention relates to treating defective, diseased, damaged or ischemic tissues or organs in a subject, preferably a human, by injecting or implanting decellularized bone marrow extracellular matrix into the subject. More particularly, the invention is directed to a medical device, preferably a stent or an artificial heart, comprising decellularized bone marrow extracellular matrix for implantation into a subject. Methods for manufacturing and coating a surface of the medical device with decellularized bone marrow extracellular matrix are also provided. The invention further relates to a biocompatible material, preferably a tissue regeneration scaffold, comprising decellularized bone marrow extracellular matrix.

2. BACKGROUND OF THE INVENTION

The healing of damaged or diseased tissues or organs is, in general, imperfect, resulting in scarring and loss of function. The ineffectiveness of pharmacological therapy has led physicians to resort to reconstructive surgery that repairs or reconstitutes soft tissue or skin by introducing an injectable or implantable material. For example, silicon gel, polyester fiber, and polytetrafluoroethylene (PTFE) have been extensively used as implants designed to replace diseased or damaged body parts. Other products that have been injected into the human body to correct soft tissue and skin defects include paraffin, petrolatum, vegetable oils, lanolin, and bees wax. Implantation or injection of these synthetic materials, however, can become hazardous to the health of the patient due to leakage, calcium deposit, hematoma, nodules, cellulitis, skin ulcers, and the triggering of autoimmune diseases (e.g., joint swelling and flu-like symptoms).

To reduce immune response caused by the injection or implantation of non-biocompatible materials, hyaluronic acid gel, a non-animal biomaterial, has been used for soft tissue augmentation (Lupton J. and Alster T., 2000, *Dermatol. Surg.* 26:135-7). Bovine collagen has also gained widespread use as an injectable material for soft tissue augmentation. Collagen is the principal extracellular matrix structural protein. Early collagen implants are often solid collagen masses which were cross-linked with chemical agents, radiation or other means to improve mechanical properties, decrease immunogenicity and/or increase resistance to resorption (see, e.g., Oliver R. et al., 1976, *Clin. Orthop.* 115:291-30; 1980, *Br. J. Exp. Path.* 61:544-549; 1981, *Conn. Tissue Res.* 9:59-62). The main problems associated with solid implants, however, are that they must be implanted surgically and often lose flexibility due to continuing cross-linking in situ. In contrast, while injectable collagen implant materials might have improved volume consistency and resistance to physical deformation, they are expensive and time consuming to prepare.

Also, engineered tissue has been used to augment existing tissue. Tissue engineering is an emerging field that studies the repair or regeneration of damaged or diseased tissues or failing or aging body parts with laboratory-grown parts such as bone, cartilage, blood vessels, and skin. Tissue engineering is based upon a relatively simple concept. First, some building material (e.g., extracellular matrix or biodegradable polymer) is shaped as needed (e.g., scaffold), seeded with living cells (e.g., stem cells), and bathed with growth factors. While the cells multiply, they fill up the scaffold and grow into a three-dimensional tissue. Once implanted in the body, the tissue will function as a substitute for the damaged tissue. As blood vessels attach themselves to the new tissue, the scaffold dissolves, and the newly grown tissue eventually blends in with its surroundings.

In response to the need for more efficient and effective implant materials, extracellular matrix (ECM) and other acellular biomaterials have been used as therapeutic scaffolds for cell attachment and proliferation and as templates for tissue repair (Schmidt C. and Baier J., 2000, *Biomaterials* 21:2215-31). Extracellular matrix is a complex structural entity surrounding and supporting cells. The extracellular matrix is found within mammalian tissues and is made up of three major classes of biomolecules: structural proteins (e.g., collagen and elastin), specialized proteins (e.g., fibrillin, fibronectin, and laminin), and proteoglycans (e.g., glycosaminoglycans). Although the exact mechanisms through which ECM facilitates repair or regeneration are not known, the composition and the organization of the components are considered to be important factors that influence cell attachment, gene expression patterns, and cell differentiation.

Successful implants include extracellular matrix from decellularized skin, blood vessels, and submucosal tissue. Abatangelo et al. in International Publication No. WO 97/18842 describes the preparation of skin substitutes in vitro by seeding keratinocytes with extracellular matrix secreted by bone marrow stem cells partially or completely differentiated into a specific connective tissue. Naughton in U.S. Pat. No. 5,830,708 describes methods for soft tissue augmentation by injecting extracellular matrix proteins secreted from fibroblasts which were grown on a three-dimensional framework. Bell in U.S. Pat. No. 5,800,537 describes a method for producing tissues for grafting using fragmented extracellular matrix particulates.

Bone marrow ECM is a part of the microenvironment that supports hematopoietic development in the bone marrow. Bone marrow ECM consists of accessory cells, cytokines, and extracellular matrix. The extracellular matrix in the bone marrow is comprised mainly of fibronectin, hemonectin, thrombospondin, collagen, laminin and glycosaminoglycans, heparan sulfate, dermantan, chondrotin sulfate (CS), and hyaluronic acid (HA). Recent findings show bone marrow is a source of multipotent adult stem cells (Jiang et al., 2002, *Exp. Hematol.* 30:826-904). The ability to interact positively with stem cells is especially important for improving the healing of tissues, such as but not limited to epithelium tissues, connective tissues, muscle tissues, and nerve tissues.

Restenosis is a closure, re-narrowing or blockage of a peripheral or coronary artery at the same site caused by an effort to open an occluded portion of the artery by angioplasty (a balloon procedure to open an obstruction or narrowing of a blood vessel) or stent (an expandable, slotted metal tube, inserted into a vessel) procedure. Restenosis occurs in 40-50% of patients have angioplasty and in 20-30% with the use of stents (Ino T. et al., 1997, *Acta. Paediatr.* 86:367-71). Restenosis has previously been addressed by providing stents which are seeded with endothelial cells that had undergone retrovirus-mediated gene transfer for either bacterial beta-galactosidase or human tissue-type plasminogen activator (Dichek D. et al. in 1989, *Circulation* 80:1347-53) or stents coated with antiplatelet agents, anticoagulant agents, antimicrobial agents, antimetabolic agents (U.S. Pat. No. 5,102,417; International Publication No. WO 90/13332). Given the ability of bone marrow ECM to improve healing of tissue, the use of bone marrow ECM as a therapy is likely to improve patient outcome for occluded arteries.

The present inventors have surprisingly found that bone marrow ECM can be isolated, is a rich source of matrix proteins and growth factors, and that injecting or implanting bone marrow extracellular matrix guides tissue repair and regeneration in injured tissue. It is therefore an object of the present invention to provide a pharmaceutical composition, a medical device, as well as a tissue regeneration scaffold comprising a therapeutically significant amount of decellularized bone marrow extracellular matrix.

3. SUMMARY OF THE INVENTION

To achieve the aforementioned objectives, we have invented a composition comprising decellularized bone marrow extracellular matrix, wherein the bone marrow extracellular matrix has been produced in vivo in an animal, preferably a mammal. The composition can be injectable or implantable. Preferably, the decellularized bone marrow extracellular matrix is prepared so the structure of the bone marrow extracellular matrix is maintained after it is decellularized.

In particular, the invention relates to methods for preparing decellularized bone marrow extracellular matrix from a bone marrow sample that has been produced in vivo. The bone marrow may be biologically, chemically, pharmaceutically, physiologically and/or mechanically modified prior to decellularization (see U.S. application Ser. No. 10/662,923, filed on even date herewith, which is incorporated by reference in its entirety for all purposes).

The bone marrow sample, which comprises an extracellular matrix and a non-extracellular matrix component, is decellularized using a combination of physical, chemical, and biological steps. During the step(s) of decellularization, the bone marrow sample is processed so at least some of the non-extracellular matrix component is removed and the remaining extracellular matrix is sterilized. Non-extracellular matrix components include, but is not limited to, cells, cell components, blood, bone spicules, extracellular matrix antigens, cytokines, serum, and fat.

Preferably, the decellularized bone marrow extracellular matrix is further treated with enzymes to remove nucleic acids and proteins. More preferably, the decellularized bone marrow extracellular matrix is further processed to limit generation of new immunological sites and to promote subsequent repopulation of the extracellular matrix with cells from a recipient after implantation of the decellularized bone marrow extracellular matrix into the recipient. The decellularized bone marrow extracellular matrix may also be dried, concentrated, lyophilized, or cryopreserved. Preferably, the decellularized bone marrow extracellular matrix is suspended in a saline solution as a final product.

The composition comprising decellularized extracellular matrix may further comprise a biological material useful for repairing, regenerating or strengthening tissues. Examples of the biological material include, but are not limited to, erythropoietin (Epo), stem cell factor (SCF), vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factor (CGF), stem cell factor (SCF), platelet-derived growth factor (PDGF), endothelial cell growth supplement (ECGS), colony stimulating factor (CSF), growth differentiation factor (GDF), integrin modulating factor (IMF), calmodulin (CaM), thymidine kinase (TK), tumor necrosis factor (TNF), growth hormone (GH), bone morphogenic proteins (BMP), matrix metalloproteinase (MMP), tissue inhibitor matrix metalloproteinase (TIMP), interferon, interleukins, cytokines, integrin, collagen, elastin, fibrillins, fibronectin, laminin, glycosaminoglycans, vitronectin, proteoglycans, transferrin, cytotactin, tenascin, and lymphokines.

The invention also relates to the injection or implantation of decellularized bone marrow extracellular matrix into a subject, preferably a human, to treat, manage or prevent the occurrence of defective, diseased, damaged or ischemic tissues or organs. The defective, diseased, damaged or ischemic tissue or organ may result from or is associated with burns, ulcer, wound, bond fracture, diabetes, psoriasis, arthritis, asthma, cystitis, inflammation, infection, ischemia, restenosis, stricture, atherosclerosis, occlusion, stroke, trauma, infarct, vascular disorders, hemophilia, cancer, organ failure (e.g., heart, kidney, lung, liver, intestine), etc. The decellularized bone marrow extracellular matrix can be injected or implanted alone or in conjunction with other therapeutically or prophylactically effective agents or methods to repair, regenerate or strengthen tissues or organs. Preferably, the injected or implanted decellularized bone marrow extracellular matrix is biocompatible. More preferably, the decellularized bone marrow extracellular matrix minimizes or avoids immune response when injected or implanted into a subject. Most preferably, the ECM is sterile and is treated with an antibacterial substance.

The invention also relates to a medical device comprising decellularized bone marrow extracellular matrix. Preferably, the medical device is a stent or an artificial heart. The decellularized bone marrow extracellular matrix can be coated, preferably by spraying or rolling, onto a surface of the medical device. The decellularized bone marrow extracellular matrix can also be used to form a structural component of the medical device. The decellularized bone marrow extracellular matrix can be used alone or in combination with a biologically active material, preferably paclitaxel, or other polymers to coat or form the medical device. The medical device is suitable for insertion in to a subject, preferably a human.

The invention further relates to a tissue regeneration scaffold comprising decellularized bone marrow extracellular matrix and methods of making the tissue regeneration scaffold.

5. DETAILED DESCRIPTION OF THE INVENTION

The present invention relates to decellularized bone marrow extracellular matrix obtained from a bone marrow sample comprising an extracellular matrix and a non-extracellular matrix component. The bone marrow sample is decellularized using at least a physical, chemical and/or biological step(s), wherein at least some of the non-extracellular matrix component is removed.

Non-extracellular matrix component includes, without limitation, cells, cellular component (e.g., cellular lipids, cellular polysaccharides, cellular debris), antigens, blood, bone spicules, serum, and fat. In preferred embodiments, at least 10%, at least 20%, at least 30%, at least 40%, at least 50%, at least 60%, at least 70%, at least 80%, at least 90%, at least 95%, at least 98%, at least 99% by weight, by volume or by size of the non-extracellular matrix component is removed.

The remaining decellularized extracellular matrix contains components which serve to attract stem cells to the site and/or provide a substrate and/or soluble factors which will promote the repair, regeneration and/or strengthening of tissues. Preferably, the decellularized bone marrow extracellular matrix is microstructurally and biochemically intact, i.e., retains strength, resiliency, and adhesion properties.

5.1 Decellularized Bone Marrow Extracellular Matrix 5.1.1 Isolation of Bone Marrow Bone marrow (BM) is a soft, spongy tissue that fills the insides of bones. Most blood cells, including red blood cells, platelets and some white blood cells are produced in the bone marrow and are then released into the bloodstream as they become mature. Stem cells found in the bone marrow are either part of a non-adherent hematopoietic component or an adherent stromal cell component. The adherent stromal cell component includes multipotent adult progenitor cells (MAPCs) and mesenchymal stem cells (MSCs). MAPCs have the ability to differentiate into many cell types including MSCs, endothelial, epithelial and hematopoietic cells, and MSCs have the ability to self-renew by proliferation and to differentiate into differentiated stromal cells including the osteogenic, chondrogenic, adipogenic, myogenic and fibroblastic lineages (Van Damme A. et al., 2002, *Curr. Gene Ther.* 2:195-209; Verfaillie C. et al., 2002, *Hematology* (Am Soc Hematol Educ Program) 369-91).

Bone marrow represents 3-5% of the total body weight and averages about 1,500 grams in adults. The hematopoietic bone marrow is organized around the vasculature of the bone cavity. Bone marrow can be sampled relatively easily using either a needle aspirate or needle biopsy technique such as those disclosed in U.S. Pat. Nos. 4,314,565; 4,481,946; 4,486,188; 4,513,754; 4,630,616; 4,664,128; 5,012,818; 5,257,632; and 5,331,972, all of which are incorporated by reference herein in their entireties.

In a bone marrow aspiration, a special needle (usually a University of Illinois needle) is inserted beneath the skin and rotated until it penetrates the cortex, or outer covering of the bone. A small amount of marrow is suctioned out of the bone by a syringe attached to the needle.

Bone marrow biopsy may be performed immediately before or after bone marrow aspiration. The procedure is performed with a special needle, which has a hollow core, much like a leather punch. In bone marrow biopsy, the needle is inserted, rotated to the right, then to the left, withdrawn, and reinserted at a different angle. This procedure is repeated until a small chip is separated from the bone marrow.

Generally, aspiration withdraws a fluid specimen (0.5 to 500 ml) that contains suspended marrow pustule from the bone marrow and needle biopsy removes a core of actual marrow cells (not fluid). More information on the procedures required to perform and evaluate needle aspiration and biopsy of bone marrow can be found in Hodges A. and Koury M., 1996, *Clin. Lab Sci.* 9:349-53, the content of which is incorporated by reference herein in its entirety.

Bone marrow aspirations and/or bone marrow biopsies can be performed in physicians' offices, outpatient clinics and/or hospital settings. Bone marrow aspirations and/or biopsies should be carried out by trained individuals who are aware of the indications, contraindications, and hazards of the procedure. The operators should follow a standard operating procedure and make an adequate assessment beforehand of clinical and hematological features (e.g., temperature, heart rate, respiration, and blood pressure). For the patient's comfort and safety, the posterior iliac crest is generally the preferred site of aspiration. Other common sites include the pelvic bone or the breastbone. The site of puncture should be cleansed first with an antiseptic solution, and the subject given a local anesthetic.

Bone marrow may also be obtained after a terminal procedure. In this case, all marrow is removed from the bones. This may be accomplished with the bones in place or removed from the subject. Sterile surgical or laboratory tools are used to separate the spongy bone containing the marrow from the outer cortical bone.

In preferred embodiments, the bone marrow sample is isolated from a mammal such as a non-primate (e.g., cows, pigs, horses, cats, dogs, rats etc.) or a primate (e.g., monkey and human), most preferably a human. In certain preferred embodiments, the bone marrow sample can be obtained from marrow which has been modified (e.g., manipulation of cells in bone marrow to alter the ECM produced by host cells). In specific embodiments, the bone marrow sample is obtained from a bone that has been conditioned to produce an amount of a biological material that is in an amount different than that produced by a bone absent the conditioning. The bone may be conditioned before or after the bone marrow is harvested.

5.1.2 Decellularization Procedures

Decellularization generally refers to the removal of non-extracellular matrix components, i.e., cells, cellular components, and other non-extracellular matrix components (e.g., blood, antigens, serum, fat) while leaving intact an extracellular matrix component. Preferably, all or substantially all of the cells, cellular components, and non-extracellular components are removed. The macroscopic structure of the ECM does not need to be maintained. However, in preferred embodiments, the microstructure of the extracellular matrix is retained after the bone marrow extracellular matrix is decellularized.

It is believed that the process of decellularization can reduce or eliminate the immune response associated with the cells as well as the cellular components. Acellular vascular tissues have been suggested to be ideal natural biomaterials for tissue repair and engineering (Schmidt C. and Baier J., supra). Bell in U.S. Pat. No. 5,800,537 describes a method for producing extracellular matrix particulates first by manually and mechanically mincing a tissue source, second by removing the cell remnants from the extracellular matrix of the tissue source in the absence of a high salt solution, and finally by fragmenting the processed extracellular matrix.

A bone marrow sample consists of cells, blood, bone spicules, fat, and extracellular matrix. The bone marrow sample may be decellularized using one or more physical, chemical and/or biological techniques to remove the cells, blood, bone spicules, and fat (see, e.g. U.S. Pat. Nos. 5,192,312; 5,613, 982; 5,632,778; 5,843,182; and 5,899,936, which are incorporated herein by reference in their entireties). The physical, chemical and/or biological methods are optimized to preserve as much as possible the composition of biologically active materials and more importantly, the microstructure of the extracellular matrix. The physical, chemical and/or biochemical techniques are to be applied in an appropriate order to purify the extracellular matrix component. The techniques described herein are preferably performed under aseptic conditions.

In certain embodiments, physical forces are used to decellularize the bone marrow samples. For example, vapor phase freezing (slow rate of temperature decline) and liquid phase freezing (rapid rate of temperature decline) can cause the formation of intracellular ice that disrupts the cells. Colloid-forming materials may be added during freeze-thaw cycles to alter ice formation patterns in the samples. Polyvinylpyrrolidone (10% w/v) and dialyzed hydroxyethyl starch (10% w/v) may be added to standard cryopreservation solutions (DMEM, 10% DMSO, 10% fetal bovine serum) to reduce extracellular ice formation while permitting formation of intracellular ice (see U.S. Pat. No. 5,613,982). The ruptured cell and resulting cellular debris can be removed by any one or more of the physical, chemical and/or biological techniques described herein.

Similarly, extracellular matrix may be isolated from bone marrow samples using centrifugation. For example, a bone marrow sample is centrifuged with a liquid preparation, preferably Histopaque and more preferably water or saline, which physically separates components of different densities. In a preferred embodiment, the speed for centrifugation ranges from 100 to 10,000 g, and more preferably, from 2,500 to 7,500 g, for between 5 to 20 minutes.

Alternatively, extracellular matrix may be isolated from bone marrow samples using filtration. For example, a bone marrow sample may be filtered using filters of specific pore size. In a specific embodiment, the filter is of a pore size, preferably of 70 to 250 µm, that allows the extracellular matrix to pass through. In another specific embodiment, the filter is of a pore size, preferably of 0.1 to 100 µm, that retains the extracellular matrix and larger components. Filtration is carried out in one step or a series of steps.

It has been reported that modification of the magnitude of the membrane dipole potential using compounds such as cholesterol, phloretin, and 6-ketocholestanol may also influence binding capacity and disrupts membrane domains. (Asawakam T. et al., 2001, *J. Biol. Chem.* 276:38457-63). Accordingly, the present invention further relates to methods for physically decellularizing bone marrow sample by agitating cellular membrane potential using electrical (e.g., voltage) means.

Other physical techniques that can be used to decellularize a bone marrow sample include, but are not limited to, mincing, rinsing, agitation, sedimentation, dialysis, cutting, grinding, pressing, electrical stimulation, electromagnetic forces, hydrostatic or hydrodynamic forces, blasting with sound waves, and ultrasonication.

In certain other embodiments, bone marrow samples may be decellularized using at least a chemical technique. In one embodiment, a bone marrow sample is treated with a solution effective to lyse native cells. Preferably, the solution may be an aqueous hypotonic or low ionic strength solution formulated to effectively lyse the native tissue cells. Such an aqueous hypotonic solution may be de-ionized water or an aqueous hypotonic buffer. The hypotonic lysis solution may include a buffered solution of water, pH 5.5 to 8, preferably pH 7 to 8. In preferred embodiments, the hypotonic lysis solution is free from calcium and zinc ions. Control of the temperature and time parameters during the treatment of the body tissue with the hypotonic lysis solution, may also be employed to limit the activity of proteases. Preferably, the aqueous hypotonic buffer may contain additives that provide suboptimal conditions for the activity of selected proteases, e.g., collagenase, which may be released as a result of cellular lysis. Additives such as metal ion chelators, e.g., 1,10-phenanthroline and ethylenediaminetetraacetic acid (EDTA), create an environment unfavorable to many proteolytic enzymes.

Accordingly, in preferred embodiments, the bone marrow sample is treated with protease inhibitors. General inhibitor solutions manufactured by Sigma and Genotech are preferred. Specifically, 4-(2-aminoethyl)-benzene-sulfonyl fluoride, E-64, bestatin, leopeptin, aprotin, PMSF, Na EDTA, TIMPs, pepstatin A, phosphoramidon, and 1,10-phenanthroline are non-limiting examples of preferred protease inhibitors.

In certain other embodiments, the bone marrow sample is treated with a detergent. In a specific embodiment, the bone marrow sample is treated with an anionic detergent, preferably sodium dodecyl sulfate in buffer. In another specific embodiment, the bone marrow sample is treated with a nonionic detergent, such as Triton X-100 or 1% octyl phenoxyl polyethoxyethanol, to solubilize cell membranes and fat. In a preferred embodiment, the bone marrow sample is treated with a combination of different classes of detergents, for example, a nonionic detergent, Triton X-100, and an anionic detergent, sodium dodecyl sulfate, to disrupt cell membranes and aid in the removal of cellular debris.

Steps should be taken to eliminate any residual detergent levels in the extracellular matrix, so as to avoid interference with the latter's ability to repair, regenerate or strengthen defective, diseased, damaged or ischemic tissues or organs. Selection of detergent type and concentration will be based partly on its preservation of the structure, composition, and biological activity of the extracellular matrix.

Extracellular matrix may also be isolated from a bone marrow sample using at least a biological technique. Preferably, the enzyme treatment limits the generation of new immunological sites. For instance, extended exposure of the bone marrow sample to proteases such as trypsin result in cell death. However, because at least a portion of the type I collagen molecule is sensitive to a variety of proteases, including trypsin, this may not be the approach of choice for collagenous grafts intended for implant in high mechanical stress locations.

In one embodiment, the bone marrow sample is treated with nucleases to remove DNA and RNA. Nucleases are effective to inhibit cellular metabolism, protein production, and cell division without degrading the underlying collagen matrix. Nucleases that can be used for digestion of native cell DNA and RNA include both exonucleases and endonucleases. A wide variety of which are suitable for use in this step of the process and are commercially available. For example, exonucleases that effectively inhibit cellular activity include DNase I and RNase A (SIGMA Chemical Company, St. Louis, Mo.) and endonucleases that effectively inhibit cellular activity include EcoR I (SIGMA Chemical Company, St. Louis, Mo.) and Hind III (SIGMA Chemical Company, St. Louis, Mo.). It is preferable that the selected nucleases are applied in a physiological buffer solution which contains ions, such as magnesium and calcium salts, which are optimal for the activity of the nuclease. It is also preferred that the ionic concentration of the buffered solution, the treatment temperature, and the length of treatment are selected to assure the desired level of effective nuclease activity. The buffer is preferably hypotonic to promote access of the nucleases to the cell interiors.

Other enzymatic digestion may be suitable for use herein, for example, enzymes that disrupt the function of native cells in the bone marrow sample may be used. For example, phospholipase, particularly phospholipases A or C, in a buffered solution, may be used to inhibit cellular function by disrupting cellular membranes of endogenous cells. Preferably, the enzyme employed should not have a detrimental effect on the extracellular matrix protein. The enzymes suitable for use may also be selected with respect to inhibition of cellular integrity, and also include enzymes which may interfere with cellular protein production. The pH of the vehicle, as well as the composition of the vehicle, will also be adjusted with respect to the pH activity profile of the enzyme chosen for use. Moreover, the temperature applied during application of the enzyme to the tissue should be adjusted in order to optimize enzymatic activity.

In another embodiment, the bone marrow sample is treated so the cells are removed using immunomagnetic bead separation techniques directed to cell surface markers (e.g., integrins, lineage markers, stem cell markers). Immunomagnetic separation (IMS) technology can isolate strains possessing specific and characteristic surface antigens (Olsvik O. et al., 1994, *Clin. Microbiol. Rev.* 7:43-54). Commercially available immunomagnetic separation processes such as Cell Release™ (Sigris Research, Brea, Calif.) was developed to address the need for a fast, general-purpose way to detach intact cells from beads after immunomagnetic separation.

Subsequent to decellularization protocols, the resultant extracellular matrix is washed at least once with suitable chemical solutions, such as saline, protease, enzymes, detergents, alcohols, acidic or basic solutions, salt solutions, EDTA, etc., to assure removal of cell debris which may include cellular protein, cellular lipids, and cellular nucleic acid, as well as any extracellular debris such as lipids and proteoglycans. Removal of the cellular and extracellular debris reduces the likelihood of the extracellular matrix eliciting an adverse immune response from the recipient upon injection or implantation. For example, the tissue may be incubated in a balanced salt solution such as Hanks' Balanced Salt Solution (HBSS), preferably sterile. The washing process may include incubation at a temperature of between about 2° C. and 42° C., with 4° C. to 25° C. most preferable. The transplant tissue matrix may be incubated in the balanced salt wash solution for up to a day, 3 days, 5 days, a week, two weeks, or a month, with changes in wash solution every second or third day. The composition of the balanced salt solution wash, and the conditions under which it is applied to the transplant tissue matrix may be selected to diminish or eliminate the activity of the nuclease or other enzyme utilized during the decellularization process.

Optionally, an antibacterial, an antifungal or a sterilant or a combination thereof, may be included in the balanced salt wash solution to protect the decellularized bone marrow extracellular matrix from contamination with environmental pathogens. In certain embodiments, the decellularized bone marrow ECM is sterilized by irradiation, ultraviolet light exposure, ethanol incubation (70-100%), treatment with glutaraldehyde, peracetic acid (0.1-1% in 4% ethanol), chloroform (0.5%), or antimycotic and antibacterial substances.

The decellularized bone marrow extracellular matrix prepared in accordance with the above is preferably free or substantially free of its native cells, and additionally, cellular and extra-cellular antigen components have been washed out of the extracellular matrix. Preferably, the decellularized bone marrow has been treated in a manner which limits the generation of new immunological sites in the collagen matrix. The ECM is obtained as a slurry of small particles. This slurry, including the slurry solution, may eventually be processed into an implant.

In addition, the decellularized extracellular matrix may contain a significant portion of the original tissue mass retaining physical properties in regard to strength and elasticity and has components which are largely collagens but also comprise glycosaminoglycans and proteins closely associated with collagen such as the basement membrane complex, laminin and fibronectin.

The above physical, chemical, and biological techniques may also be used to remove non-extracellular matrix components (e.g., cells, cellular components, blood, bone spicules, extracellular matrix antigens, serum, fat, etc.) prior to removal from the bone marrow cavity. For example, one or more solutions may be perfused through the bone marrow, as blood does normally, to solubilize or force non-extracellular matrix components out of the marrow. More specifically, de-ionized water, a detergent solution, an enzymatic solution (e.g., trypsin, dispase, DNase) or EDTA can be forced through the marrow cavity to remove cells, cell debris, blood or fat prior to harvesting the bone marrow samples.

One aspect of the invention further provides the preservation of the decellularized bone marrow extracellular matrix for later use. The decellularized bone marrow extracellular matrix can be freeze-dried for prolonged storage. Likewise, the decellularized bone marrow extracellular matrix can be air-dried by any known standard techniques. In one embodiment, the decellularized bone marrow extracellular matrix can be concentrated or dehydrated and later reconstituted or rehydrated, respectively, before use.

In yet another embodiment, the decellularized bone marrow extracellular matrix can be lyophilized. The lyophilized ECM may be in the form of an implant which has pores. Characteristics of the pore structure can be controlled by process parameters. In yet another embodiment, the decellularized bone marrow extracellular matrix can be formed as a gel. Preferably, the proteins are temporarily and reversibly denatured. In yet another embodiment, the decellularized bone marrow extracellular matrix can be precipitated or co-precipitated with other proteins or biologics.

In certain embodiments, the decellularized bone marrow extracellular matrix is cryopreserved. For general methods of cryopreservation see Brockbank K., *Basic Principles of Viable Tissue Preservation. In: Transplantation Techniques and Use of Cryopreserved Allograft Cardiac Valves and Vascular Tissue*. D. R. Clarke (ed.), Adams Publishing Group, Ltd., Boston. pp 9-23, which is hereby incorporated by reference herein in its entirety. Cryopreservation of decellularized bone marrow extracellular matrix would assure a supply or inventory of substantially non-immunogenic extracellular matrices which, upon thawing, would be ready for further treatment according to the subsequent steps of this invention, or further processed as desired to provide an implant tissue product.

In another particular embodiment, the decellularized bone marrow extracellular matrix is treated to enhance the ingrowth and attachment of the recipient's own cells. Growth factors, cytokines, genetic material, etc., for example, can be used to incubate the decellularized extracellular matrix prior to its injection or implantation into a subject or prior to its coating on or incorporation into a medical device. Preferred growth factors include, but are not limited to, erythropoietin (Epo), endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factor (CGF), stem cell factor (SCF), platelet-derived growth factor (PDGF), endothelial cell growth supplement (ECGS), colony stimulating factor (CSF), growth differentiation factor (GDF), integrin modulating factor (IMF), calmodulin (CaM), thymidine kinase (TK), growth hormone (GH), bone morphogenic proteins (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16), matrix metalloproteinase (MMP), and tissue inhibitor matrix metalloproteinase (TIMP). Preferred cytokines include, but are not limited to, interleukins (e.g., IL-1, IL-2, IL-3, IL-4, IL-5, IL-6, IL-7, IL-8, IL-9, IL-10, IL-11, IL-12, IL-15), lymphokines, tumor necrosis factor (TNF) (e.g., TNF-α, TNF-β), and interferons.

5.2 Therapeutic Use

The invention relates generally to the use of decellularized bone marrow extracellular matrix to repair or regenerate defective, diseased, damaged or ischemic tissues or organs in a subject. Pharmaceutical compositions, medical devices and tissue regeneration scaffolds comprising decellularized bone marrow extracellular matrix can be injected or implanted into a subject in need thereof.

In certain embodiments, the decellularized bone marrow extracellular matrix may be used to treat defective, diseased, damaged or ischemic tissues or organs which include, but are not limited to, head, neck, eye, mouth, throat, esophagus, chest, bone, ligament, cartilage, tendons, lung, colon, rectum, stomach, prostate, breast, ovaries, fallopian tubes, uterus, cervix, testicles or other reproductive organs, hair follicles, skin, diaphragm, thyroid, blood, muscles, bone marrow, heart, lymph nodes, blood vessels, large intestine, small intestine, kidney, liver, pancreas, brain, spinal cord, and the central nervous system.

In particular, the decellularized bone marrow extracellular matrix may be used to treat diseases that may benefit from improved angiogenesis, cell proliferation and tissue regeneration. Such diseases or conditions include, but are not limited to, burns, ulcer, wound, bone fracture, diabetes, psoriasis, arthritis, asthma, cystitis, inflammation, infection, ischemia, restenosis, stricture, atherosclerosis, occlusion, stroke, trauma, infarct, vascular disorders, hemophilia, cancer, and organ failure (e.g., heart, kidney, lung, liver, intestine, etc.).

In a specific embodiment, the present invention regenerates or replaces at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, at least 10%, at least 5%, or at least 1% of defective, diseased, damaged or ischemic cells from the affected tissue or organ.

The methods of the present invention is provided for an animal, including but not limited to mammals such as a non-primate (e.g., cows, pigs, horses, chickens, cats, dogs, rats, etc.) and a primate (e.g., monkey such as a cynomolgous monkey and a human). In a preferred embodiment, the subject is a human.

The decellularized bone marrow extracellular matrix is useful alone or in combination with other treatment modalities. In certain embodiments, the treatment of the present invention further includes the administration of one or more immunotherapeutic agents, such as antibodies and immunomodulators, which include, but are not limited to, HERCEPTIN®, RITUXAN®, OVAREX™, PANOREX®, BEC2, IMC-C225, VITAXIN™, CAMPATHR®, I/H, Smart M195, LYMPHOCIDE™, Smart I D10, ONCOLYM™, rituximab, gemtuzumab, or trastuzumab. In certain other embodiments, the treatment method further comprises hormonal treatment. Hormonal therapeutic treatments comprise hormonal agonists, hormonal antagonists (e.g., flutamide, tamoxifen, leuprolide acetate (LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

5.2.1 Pharmaceutical Compositions

The decellularized bone marrow extracellular matrix can be formulated into pharmaceutical compositions that are suitable for administration to a subject. Such compositions comprise a prophylactically or therapeutically effective amount of the decellularized bone marrow extracellular matrix as disclosed herein, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete) or, more preferably, MF59C.1 adjuvant available from Chiron, Emeryville, Calif.), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Other examples of suitable pharmaceutical vehicles are described in "Remington: the Science and Practice of Pharmacy", 20th ed., by Mack Publishing Co. 2000.

Generally, the ingredients of compositions of the invention are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed from an infusion bottle containing sterile pharmaceutical grade water or saline. Where the composition is administered by injection, an ampule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Various delivery systems are known and can be used to administer the compositions of the invention, e.g., encapsulation in liposomes, microparticles, microcapsules, receptor-mediated endocytosis (see, e.g., Wu and Wu, 1987, *J. Biol. Chem.* 262:4429-4432), etc. Methods of administering a prophylactic or therapeutic amount of the compositions of the invention include, but are not limited to, parenteral administration (e.g., intradermal, intramuscular, intraperitoneal, intravenous and subcutaneous), epidural, and mucosal (e.g., intranasal, inhaled, and oral routes). Preferably, a prophylactic or therapeutic amount of the compositions of the invention is directly injected at the defective, diseased, damaged or ischemic tissue. The composition comprising decellularized extracellular matrix of conditioned body tissue may be administered by any convenient route, for example, by infusion or bolus injection, by absorption through epithelial or mucocutaneous linings (e.g., oral mucosa, rectal and intestinal mucosa, etc.) and may be administered together with other biologically active agents, preferably paclitaxel. Administration can be systemic or local. In addition, it may be desirable to introduce the pharmaceutical composition of the invention into the central nervous system by any suitable route, including intraventricular and intrathecal injection; intraventricular injection may be facilitated by an intraventricular catheter, for example, attached to a reservoir, such as an Ommaya reservoir.

In another embodiment, the decellularized bone marrow extracellular matrix can be delivered in a controlled release or sustained release system. In one embodiment, a pump may be used to achieve controlled or sustained release (see Langer, 1990, *Science* 249:1527-1533; Sefton, 1987, *CRC Crit. Ref. Biomed. Eng.* 14:20; Buchwald et al., 1980, *Surgery* 88:507; Saudek et al., 1989, *N. Engl. J. Med.* 321:574). Any technique known to one of skill in the art can be used to produce sustained release formulations comprising the decellularized extracellular matrix of the invention. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760, each of which is incorporated herein by reference in its entirety.

In another embodiment, polymeric materials can be used to achieve controlled or sustained release of the decellularized extracellular matrix material (see, e.g., *Medical Applications of Controlled Release*, Langer and Wise (eds.), CRC Pres., Boca Raton, Fla. (1974); *Controlled Drug Bioavailability*, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105); U.S. Pat. Nos. 5,679,377; 5,916,597; 5,912,015; 5,989,463; and 5,128,326; International Publication Nos. WO 99/15154 and WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glucosides) (PLGA), and polyorthoesters. In a preferred embodiment, the polymer used in a sustained release formulation is inert, free of leachable impurities, stable during storage, sterile, and biodegradable. In yet another embodiment, a controlled or sustained release system can be placed in proximity to the target, thus requiring only a fraction of the systemic dose (see, e.g., Goodson, 1984, in *Medical Applications of Controlled Release*, supra, vol. 2, pp. 115-138).

The amount of the pharmaceutical composition which will be effective in the treatment of a particular disorder or condition will depend on the nature of the disorder or condition, and can be determined by standard clinical techniques. In addition, in vitro assays and animal models may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

5.2.2 Medical Devices

The decellularized bone marrow extracellular matrix of the invention may also be used to form a medical or prosthetic device, preferably a stent or an artificial heart, which may be implanted in the subject. More specifically, the decellularized bone marrow extracellular matrix of the invention may be incorporated into the base material needed to make the device. For example, in stent comprising a sidewall of elongated members or wire-like elements, the decellularized bone marrow extracellular matrix can be used to form the elongated members or wire-like elements. On the other hand, the decellularized bone marrow extracellular matrix can be used to coat or cover the medical device.

The medical devices of the present invention may be inserted or implanted into the body of a patient.

5.2.2.1 Types of Medical Device

Medical devices that are useful in the present invention can be made of any biocompatible material suitable for medical devices in general which include without limitation natural polymers, synthetic polymers, ceramics and metallics. Metallic material is more preferable. Suitable metallic materials include metals and alloys based on titanium (such as nitinol, nickel titanium alloys, thermo-memory alloy materials), stainless steel, tantalum, nickel-chrome, or certain cobalt alloys including cobalt-chromium-nickel alloys such as Elgiloy® and Phynox®. Metallic materials also include clad composite filaments, such as those disclosed in WO 94/16646.

Metallic materials may be made into elongated members or wire-like elements and then woven to form a network of metal mesh. Polymer filaments may also be used together with the metallic elongated members or wire-like elements to form a network mesh. If the network is made of metal, the intersection may be welded, twisted, bent, glued, tied (with suture), heat sealed to one another; or connected in any manner known in the art.

The polymer(s) useful for forming the medical device should be ones that are biocompatible and avoid irritation to body tissue. They can be either biostable or bioabsorbable. Suitable polymeric materials include without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Other polymers that are useful as materials for medical devices include without limitation dacron polyester, poly (ethylene terephthalate), polycarbonate, polymethylmethacrylate, polypropylene, polyalkylene oxalates, polyvinylchloride, polyurethanes, polysiloxanes, nylons, poly (dimethyl siloxane), polycyanoacrylates, polyphosphazenes, poly(amino acids), ethylene glycol I dimethacrylate, poly (methyl methacrylate), poly(2-hydroxyethyl methacrylate), polytetrafluoroethylene poly(HEMA), polyhydroxyalkanoates, polytetrafluorethylene, polycarbonate, poly(glycolide-lactide) co-polymer, polylactic acid, poly(ε-caprolactone), poly(β-hydroxybutyrate), polydioxanone, poly(γ-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., RGD, in which the polymers retain their structural integrity while allowing for attachment of cells and molecules, such as proteins, nucleic acids, and the like.

Furthermore, although the invention can be practiced by using a single type of polymer to form the medical device, various combinations of polymers can be employed. The appropriate mixture of polymers can be coordinated to produce desired effects when incorporated into a medical device. In certain preferred embodiments, the decellularized extracellular matrix is mixed with a polymer.

The decellularized bone marrow extracellular matrix of the invention may also be used alone or in combination with a polymer described above to form the medical device such as through formation of a composite material. The decellularized bone marrow extracellular matrix may be dried to increase its mechanical strength. The dried decellularized bone marrow extracellular matrix may then be used as the base material to form a whole or part of the medical device. In preferred embodiments, the decellularized bone marrow extracellular matrix constitutes at least 5%, at least 10%, at least 25%, at least 50%, at least 80%, at least 90%, at least 95%, at least 99% by weight or by size of the medical device.

Examples of the medical devices suitable for the present invention include, but are not limited to, stents, surgical staples, catheters (e.g., central venous catheters and arterial catheters), guidewires, cannulas, cardiac pacemaker leads or lead tips, cardiac defibrillator leads or lead tips, implantable vascular access ports, blood storage bags, blood tubing, vascular or other grafts, intra-aortic balloon pumps, heart valves, cardiovascular sutures, total artificial hearts and ventricular assist pumps, and extra-corporeal devices such as blood oxygenators, blood filters, hemodialysis units, hemoperfusion units and plasmapheresis units.

Medical devices of the present invention include those that have a tubular or cylindrical-like portion. The tubular portion of the medical device need not to be completely cylindrical. For instance, the cross-section of the tubular portion can be any shape, such as rectangle, a triangle, etc., not just a circle. Such devices include, without limitation, stents and grafts. A bifurcated stent is also included among the medical devices which can be fabricated by the method of the present invention.

Medical devices which are particularly suitable for the present invention include any kind of stent for medical purposes which is known to the skilled artisan. Suitable stents include, for example, vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 5,449,373 issued to Pinchasik et al.

5.2.2.2 Methods of Coating the Medical Device

In the present invention, the decellularized bone marrow extracellular matrix of the invention, preferably in combination with a biologically active material such as paclitaxcel, can be applied by any method to a surface of a medical device to form a coating. Examples of suitable methods are spraying, brushing, swabbing, dipping, rolling, electrostatic deposition and all modern chemical ways of immobilization of biomolecules to surfaces. Preferably, the decellularized bone marrow extracellular matrix is applied to a surface of a medical device by spraying and rolling. In one embodiment of the present invention, more than one coating method can be used to make a medical device. In certain embodiments, the decellularized extracellular matrix is placed into a carrier in order to apply it to the device surface. Non-limiting examples of carriers include SIBS, PLGA, PGA, collagen, etc.

Furthermore, before applying the coating composition, the surface of the medical device is optionally subjected to a pre-treatment, such as roughening, oxidizing, sputtering, plasma-deposition or priming in embodiments where the surface to be coated does not comprise depressions. Sputtering is a deposition of atoms on the surface by removing the atom from the cathode by positive ion bombardment through a gas discharge. Also, exposing the surface of the device to a primer is a possible method of pre-treatment.

Coating compositions suitable for applying coating materials to the devices of the present invention can include a polymeric material and preferably a biologically active material dispersed or dissolved in a solvent suitable for the medical device, which are known to the skilled artisan. The solvents used to prepare coating compositions include ones which can dissolve the polymeric material into solution or suspend the polymeric material and do not alter or adversely impact the therapeutic properties of the biologically active material employed. For example, useful solvents for silicone include tetrahydrofuran (THF), chloroform, toluene, acetone, isooctane, 1,1,1-trichloroethane, dichloromethane, and mixture thereof.

The polymeric material should be a material that is biocompatible and avoids irritation to body tissue. Preferably the polymeric materials used in the coating composition of the present invention are selected from the following: polyurethanes, silicones (e.g., polysiloxanes and substituted polysiloxanes), and polyesters. Also preferable as a polymeric material is styrene-isobutylene-styrene (SIBS). Other polymers which can be used include ones that can be dissolved and cured or polymerized on the medical device or polymers having relatively low melting points that can be blended with biologically active materials. Additional suitable polymers include, thermoplastic elastomers in general, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM (etylene-propylene-diene) rubbers, fluorosilicones, polyethylene glycol, polysaccharides, phospholipids, and combinations of the foregoing.

More preferably for medical devices which undergo mechanical challenges, e.g. expansion and contraction, the polymeric materials should be selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating composition is capable of undergoing deformation under the yield point when the device is subjected to forces, stress or mechanical challenge.

The term "biologically active material" encompasses therapeutic agents, such as drugs, and also genetic materials and biological materials. The genetic materials mean DNA or RNA, including, without limitation, of DNA/RNA encoding a useful protein stated below, intended to be inserted into a human body including viral vectors and non-viral vectors. The biological materials include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factor (CGF), stem cell factor (SCF), platelet-derived growth factor (PDGF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen, elastin, fibrillins, fibronectin, vitronectin, laminin, glycosaminoglycans, proteoglycans, transferrin, cytotactin, and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells. Biologically active materials also include non-genetic therapeutic agents, such as:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, and acetylsalicylic acid, amlodipine and doxazosin;

anti-inflammatory agents such as glucocorticoids, betamethasone, dexamethasone, prednisolone, corticosterone, budesonide, estrogen, sulfasalazine, and mesalamine;

antineoplastic/antiproliferative/anti-miotic agents such as paclitaxel, 5-fluorouracil, cisplatin, vinblastine, cladribine, vincristine, epothilones, methotrexate, azathioprine, adriamycin and mutamycin; endostatin, angiostatin and thymidine kinase inhibitors, taxol and its analogs or derivatives;

anesthetic agents such as lidocaine, bupivacaine, and ropivacaine;

anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;

DNA demethylating drugs such as 5-azacytidine, which is also categorized as a RNA or DNA metabolite that inhibit cell growth and induce apoptosis in certain cancer cells;

vascular cell growth promoters such as growth factors, vascular endothelial growth factors (VEGF, all types including VEGF-2), growth factor receptors, transcriptional activators, and translational promoters;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin, rapamycin;

angiogenic substances, such as acidic and basic fibroblast growth factors, estrogen including estradiol (E2), estriol (E3) and 17-Beta Estradiol; and drugs for heart failure, such as digoxin, beta-blockers, angiotensin-converting enzyme (ACE) inhibitors including captopril, enalopril, and statins and related compounds.

In certain embodiments, the medical device of the present invention is covered with one coating layer. In certain other embodiments, the medical device of the present invention is covered with more than one coating layer. In preferred embodiments, the medical device is covered with different coating layers. For example, the coating can comprise a first layer and a second layer that contain different biologically active materials. Alternatively, the first layer and the second layer may contain an identical biologically active material having different concentrations. In one embodiment, either the first layer or the second layer may be free of biologically active material.

5.2.3 Tissue Regeneration Scaffold

One aspect of the invention provides for use alone or through the incorporation of the decellularized bone marrow extracellular matrix into a biocompatible material for implantation into a subject, preferably human. In a preferred embodiment, the biocompatible material is in the form of a scaffold.

The scaffold may be of decellularized bone marrow ECM or combined with natural collagen or synthetic polymer. These scaffolds may be produced by freeze-drying, air-drying, molding or salt leaching. In certain preferred embodiments, the scaffold serves as a template for cell proliferation and ultimately tissue formation. In a specific embodiment, the scaffold allows the slow release of the decellularized bone marrow extracellular matrix into the surrounding tissue. As the cells in the surrounding tissue begin to multiply, they fill up the scaffold and grow into three-dimensional tissue. Blood vessels then attach themselves to the newly grown tissue, the scaffold dissolves, and the newly grown tissue eventually blends in with its surrounding.

5.2.4 Cell Culture Substrate

Certain cell types require a substrate other than culture plastic to grow and retain proper function outside their native environment (e.g., embryonic stem cells, some neural cells). Surfaces coated with extracellular matrix proteins (e.g., laminin, fibronectin, collagen, Matrigel) have been shown to enhance the growth of certain cell types compared to the uncoated surface. Also, cells grown on top of or within three-dimensional gels or scaffolds grow and function differently than those on two-dimensional coated or uncoated surfaces.

In certain embodiments, the decellularized bone marrow extracellular matrix of the invention is used for cell culture. In one embodiment, some or all of the decellularized bone marrow extracellular matrix can be solubilized in an acidic solution, preferably 0.05 to 0.5 M acetic acid, with or without an enzyme which breaks apart the collagen molecule (e.g., pepsin, trypsin, dispase, collagenase). The resulting solution containing preferably 0.5 to 15 mg/ml of decellularized bone marrow extracellular matrix will gel when the pH is neutralized (temperature preferably between 25° C. to 40° C.). During the gelation process the solution can be added to a container to coat the exposed surfaces, seeded with cells to form a gel containing cells, or cast into sheet or slabs.

In another embodiment, a suspension of decellularized bone marrow extracellular matrix or a solution, as described above, can be dried to form a sheet of ECM or adsorbed onto a surface. The thickness will be determined by the concentration of ECM in the liquid and the volume of liquid per surface area of the container in which it is held. A glass or non-stick (e.g., Teflon, silicone) container is preferred to enable the removal of the sheet without destroying its integrity. Although not necessary, the sheet can be cross-linked prior to or after removal from the container in which it was dried. Examples of cross-linking treatments include but are not limited to UV light or other high frequency photon source, aldehydes, carbodiimides, and severe dehydration. Cells may be seeded directly onto the sterilized coated containers or onto the sheets which have been removed.

In yet another embodiment, a suspension of decellularized bone marrow extracellular matrix or a solution, as described above, can be freeze-dried within a container to form a porous coating or layer on the surface of a culture container. The ratio of freezing and concentration of ECM in the liquid will determine the pore structure and pore volume fraction. Altering these properties will allow control of those parameters. Preferably, the freezing temperature will be between −10° C. and −196° C.

6. EXAMPLES

6.1 Example 1

First, a bone marrow sample is isolated from a pig or cow. Second, the bone marrow sample is filtered to remove bone spicules. Third, the remaining bone marrow sample is centrifuged in saline to remove the fat. Fourth, a non-ionic detergent is added to the remaining bone marrow sample to solubilize the cell membranes and any remaining fat. The remaining bone marrow sample is then rinsed with saline and filtered to remove the remaining extracellular matrix components. The rinsing step is repeated at least one time. Further, the remaining bone marrow sample is further treated with DNase and RNase to breakdown remaining nucleic acids and rinsed with saline to remove the remaining extracellular matrix components. Finally, the resulting extracellular matrix is sterilized using standard techniques in the art, e.g., peracetic acid (0.1%).

6.2 Example 2

First, a bone marrow sample is removed from the bone marrow cavity and the cortical bone by cutting, scooping, chiseling or sawing. The marrow is then reduced to small pieces by cutting, grinding, chopping, shearing, or crushing. The blood components are removed by rinsing, one or more times, in buffered saline or water. Next, the bone is separated from the ECM and any other remaining components by vigorous agitation (e.g., vortexing, shaking). After allowing the bone fragments to settle to the bottom, the non-bone components are removed by carefully decanting or aspirating (e.g., pipet). This process is repeated by adding more saline or water to the remaining bone. The non-bone components are treated with a combination of non-ionic detergent, acidic solution, alcohol solution, and basic solution to solubilize non-ECM components. Alternatively, the non-blood components are treated with an acidic or enzymatic solution (0.5 M acetic acid with pepsin 1 mg/ml). The solubilized ECM components are then separated by decanted following centrifugation and filtering with a 20 to 100 micron filter. The filtered solids will contain some of the bone marrow ECM. This ECM is processed further for use by lyophilization, precipitation, or gelation.

6.3 Example 3

6.3.1 Isolation Procedure

Ribs and sternum from a freshly killed pig are collected and the cortical bone is removed. Large pieces of bone marrow are obtained by piercing, cutting and prying at the cortical bone-bone marrow interface with a sharp, stout knife. The large pieces of bone marrow are subsequently reduced in size to less than 5 mm on a side by cutting, crushing or shearing. Blood which remains in these pieces is rinsed away by multiple rinses using a buffered saline with protease inhibitor Protease-Arrest™ (Genotech, St. Louis, Mo.). For each rinse, the marrow is first placed in the solution and slowly agitated for 30 minutes. The rinsing solution is then removed from the bone marrow pieces with a pipet. Following the final rinse, more buffered saline with protease inhibitor Protease-Arrest™ is added to the bone marrow piece. The marrow is separated from the bone pieces by vigorous agitation with a standard lab vortex mixer. The resulting suspension of marrow is transferred to another container using a pipet. This process is repeated several times until the bone is substantially free of marrow.

Finally, the marrow suspension is centrifuged at about 3,000 g for 15 minutes and the supernatant is removed. Distilled water with protease inhibitor Protease-Arrest™ is added to the pellet and gently agitated to lyse and remove the cells. This suspension is filtered using a 40 micron filter. The filtered solid is collected and processed for use. Optionally, the distilled water rinse and subsequent filtering step can be repeated to remove any remaining cells or cell debris. Aseptic conditions are maintained throughout the isolation procedure.

6.3.2 Production of a Freeze-Dried Porous Scaffold 0.05 M acetic acid is added to the solid material obtained from the isolation procedure discussed above to yield 1 to 6 mg of bone marrow ECM per ml. The mixture is vortexed or homogenized until a suspension is formed. The suspension is transferred to a plastic or metal mold and placed in a −70° C. freezer for 4 hours or until frozen. Afterwards, the mold is transferred to a freeze drier and pull a vacuum of <100 mTorr. The vacuum is held at a temperature between 0° C. and 25° C. for 12 hours or until all liquid has sublimated. Optionally, the sample can be cross-linked by holding a vacuum of <300 mTorr at 110° C. for 24 hours. Prior to use, the scaffold formed in the mold is rehydrated by placing the scaffold in sterile saline at room temperature for 12 hours. Preferably, prior to rehydration, the scaffold is sterilized by first placing in 1% peracetic acid and 70% ethanol for 12 hours, and then rinsing three times in sterile saline prior to implantation.

6.4 Example 4

6.4.1 Isolation Procedure

Ribs and sternum from a freshly killed pig were collected and the cortical bone was removed. Large pieces of bone marrow were obtained by piercing, cutting, and prying at the cortical bone-bone marrow interface with a sharp, stout knife. The large pieces of bone marrow were subsequently reduced in size to less than 5 mm on a side by cutting, crushing or shearing. The bone marrow pieces were washed in a buffered saline with protease inhibitor Protease-Arrest™. A DNase solution (10 mg/ml DNase solution (Sigma), 5 mM $MgCl_2.6H_2O$, and 0.5 mM $CaCl_2$) was added to cover the bone marrow pieces. The suspension was gently shaken at 37° C. for 50 minutes. Afterwards, the DNase solution was removed and buffered saline was added. The suspension was shaken at 4° C. for 10 minutes.

The solution was removed and more buffered saline was added. The suspension was vortexed until all fibrous material was removed from the bone marrow pieces. A first supernatant was collected. More buffered saline was added to rinse the bone marrow pieces and a second supernatant was collected.

The first and second supernatant were pooled together and centrifuged at 10,000 RPM for 7 minutes. The pellet was resuspended in 1 ml DNase solution and shaken at 37° C. for 20 minutes. After centrifuging the suspension at 10,000 RPM for 7 minutes, the supernatant was discarded. Buffered saline was added and the suspension was shaken at 4° C. for 20 minutes. After centrifuging the suspension at 10,000 RPM for 7 minutes, the supernatant was again discarded. The steps of adding the buffered saline, shaking the suspension at 4° C. for 20 minutes, centrifuging at 10,000 RPM for 7 minutes, and discarding the supernatant were repeated twice. The suspension was centrifuged at 10,000 RPM for 10 minutes to collect the pellet.

6.4.2 Experimental Design

The PicoGreen® dsDNA quantification assay (Turner Bio-Systems) was used to determine the DNA content of untreated bone marrow samples in the control group and the DNase-treated bone marrow samples in the experimental group.

The Sircol™ COLLAGEN assay (Biocolor Ltd.) was used to determine the pepsin/acetic acid soluble collagen content of untreated bone marrow samples in the control group and the DNase-treated bone marrow samples in the experimental group

6.4.3 Data

Figure 1:
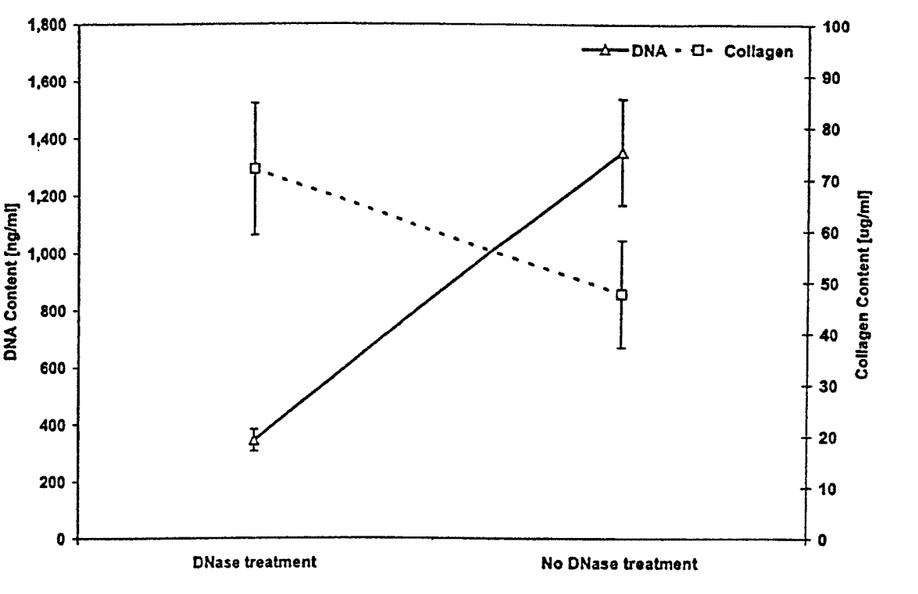
FIG. 1 is a graph showing the effect of DNase-treatment on the DNA and collagen contents of bone marrow samples.

As shown in FIG. 1, the average (n=5) DNA content of DNase treated samples was 4 times lower (p<0.005) than non-DNase-treated samples and approaches the lower detection limit for the assay. In contrast, the average (n=5) collagen content of DNase treated samples was 1.5 times higher than non-DNase-treated samples, although the difference was not significant (p=0.18).

Together, the data suggests that the isolation method described supra (Section 6.4.1) retains more collagen and causes the DNA in the bone marrow sample to be washed away or fragmented. Therefore, this isolation method lowers the overall amount of cells or cell debris in the remaining collagen or extracellular matrix.

6.4.4 Production of an Air-Dried Sheet 0.05 acetic acid is added to the solid material obtained from the isolation procedure discussed above to yield 1 to 6 mg of marrow ECM per ml. The mixture is vortexted for 5 minutes, ultrasonicated for 2 minutes, or homogenized for less than 1 minute until a suspension is formed. The suspension is transferred to a Teflon, silicone, or glass mold (1 mg/ml suspension at 1 ml/10 $cm^2$). Afterwards, the mold is transferred to a dryer and dried under a clean, sterile hood at room temperature for 72 hours. Optionally, the sample can be cross-linked by holding a vacuum of <300 mTorr at 110° C. for 24 hours. Prior to use, the scaffold formed in the mold is rehydrated by placing the scaffold in sterile saline at room temperature for 12 hours. Preferably, prior to rehydration, the scaffold is sterilized by first placing in 1% peracetic acid and 70% ethanol for 12 hours, and then rinsing three times in sterile saline prior to implantation.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings. Such modifications are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

What is claimed is:

1. A medical device comprising a composition comprising decellularized bone marrow extracellular matrix of an animal, wherein the bone marrow extracellular matrix has been produced in vivo in the animal.

2. The medical device of claim 1, wherein the non-extracellular matrix component comprises cells, cell components, antigens, cytokines, blood, bone spicules, serum, and fat.

3. The medical device of claim 1, wherein the animal is a mammal.

4. The medical device of claim 3, wherein the mammal is selected from the group consisting of a cow, a pig, a horse, a chicken, a cat, a dog, a rat, and a monkey.

5. The medical device of claim 1, wherein the method further comprises the step of enzymatically treating the decellularized bone marrow extracellular matrix.

6. The medical device of claim 1, wherein the method further comprises the step of suspending the decellularized bone marrow extracellular matrix in a saline solution.

7. The medical device of claim 1, wherein the composition further comprises a biological material, wherein the biological material is selected from the group consisting of erythropoietin, stem cell factor (SCF), vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factor (CGF), stem cell factor (SCF), platelet-derived growth factor (PDGF), endothelial cell growth supplement (ECGS), colony stimulating factor (CSF), growth differentiation factor (GDF), integrin modulating factor (IMF), calmodulin (CaM), thymidine kinase (TK), tumor necrosis factor (TNF), growth hormone (GH), bone morphogenic proteins (BMP), matrix metalloproteinase (MMP), tissue inhibitor matrix metalloproteinase (TIMP), interferon, interleukins, cytokines, integrin, collagen, elastin, fibrillins, fibronectin, laminin, glycosaminoglycans, hemonectin, thrombospondin, heparan sulfate, dermantan, chondrotin sulfate (CS), hyaluronic acid (HA), vitronectin, proteoglycans, transferrin, cytotactin, tenascin, and lymphokines.

8. The medical device of claim 1, wherein the composition further comprises a biologically active material.

9. The medical device of claim 8, wherein the biologically active material is paclitaxel.

10. The medical device of claim 1, wherein the medical device has a surface and the decellularized bone marrow extracellular matrix is coated onto the surface.

11. The medical device of claim 1, wherein the medical device comprises a sidewall comprising a wire-like element, wherein the wire-like element comprises the decellularized bone marrow extracellular matrix.

12. The medical device of claim 1, which is a stent.

13. The medical device of claim 1, wherein the decellularized bone marrow extracellular matrix is produced by a method comprising the steps of:
a. obtaining from the animal a bone marrow sample having an extracellular matrix and non-extracellular matrix components;
b. processing the bone marrow sample to remove at least some of the non-extracellular matrix components to obtain decellularized bone marrow extracellular matrix; and
c. sterilizing the decellularized bone marrow extracellular matrix.

14. The medical device of claim 13, wherein at least 50% of the non-extracellular matrix components are removed.

15. The medical device of claim 13, wherein the bone marrow extracellular matrix is arranged in a structure and wherein the structure is maintained after the bone marrow extracellular matrix is decellularized.

16. A method for treating a defective, diseased, damaged or ischemic tissue or organ in a subject comprising implanting the medical device of claim 1 into the subject.

17. A method for treating a defective, diseased, damaged or ischemic tissue or organ in a subject comprising injecting the medical device of claim 1 into the subject.

18. A method for reconstructing a tissue in a subject comprising implanting the medical device of claim 1 into the subject.

19. A method for reconstructing a tissue in a subject comprising injecting the medical device of claim 1 into the subject.

* * * * *